United States Patent
Deakter

(10) Patent No.: US 7,401,028 B2
(45) Date of Patent: Jul. 15, 2008

(54) SYSTEM AND PROCESS FOR MATCHING PATIENTS WITH CLINICAL MEDICAL TRIALS

(76) Inventor: Daniel R. Deakter, 7810 Lago Del Mar Dr., #108, Boca Raton, FL (US) 33433

( * ) Notice: Subject to any disclaimer, the term of this patent is extended or adjusted under 35 U.S.C. 154(b) by 908 days.

(21) Appl. No.: 10/290,725

(22) Filed: Nov. 8, 2002

(65) Prior Publication Data

US 2004/0093238 A1    May 13, 2004

(51) Int. Cl.
- G06F 19/00    (2006.01)
- G06F 7/00     (2006.01)
- G06Q 50/00    (2006.01)
- A61B 5/00     (2006.01)

(52) U.S. Cl. .................. 705/3; 707/3; 600/300; 705/2

(58) Field of Classification Search .......... 705/2, 705/1, 4, 3; 600/300; 707/3
See application file for complete search history.

(56) References Cited

U.S. PATENT DOCUMENTS

| 5,664,109 | A  | * | 9/1997  | Johnson et al. | 705/2 |
| 6,151,581 | A  | * | 11/2000 | Kraftson et al. | 705/3 |
| 2002/0002474 | A1 |   | 1/2002  | Michelson | 705/3 |
| 2002/0077853 | A1 | * | 6/2002  | Boru et al. | 705/2 |
| 2002/0099570 | A1 | * | 7/2002  | Knight | 705/2 |
| 2003/0097291 | A1 | * | 5/2003  | Freedman | 705/8 |

OTHER PUBLICATIONS

Baldwin, System makes it easier to link patients to clinical trials, Nov. 1998, American Medical News, pp. 25-26.*
Clinical Trials; Comprehensive Online Resource Launched, Dec. 2000, Angiogenesis Weekly, p. 20.*
TVisions Wins Top Web Extranet Award; Recognized For Creative, Life-Saving Site, Jul. 1999, p. 1.*
Veritas Medicine Launches Comprehensive Online Clinical Trials and Treatment Resource for Chronically Ill Patients and Thei Physicians, Nov. 2000, p. 1.*
Eichenwald et al., Recruiting Subjects for Drug Tests is Big Business for Doctors, May 1999, The Oregonian, p. A05.*
Dr. David Ginsberg, *The Investigator's Guide to Clinical Research*, pp. 100-106 (2002).
www.mddatacor.com "Mddatacor in the News", News Releases (Jun. 2002; Aug. 2002; and Sep. 2002).
Anonymous, "R & D Directions," How to Keep Rolling in Enrollment, Engel Publishing Partners (Scotch Plains, NJ), vol. 4 (No. 2), p. 10-11, (Mar. 1998).

* cited by examiner

*Primary Examiner*—C Luke Gilligan
*Assistant Examiner*—Rachel L Porter
(74) *Attorney, Agent, or Firm*—Bose McKinney & Evans LLP

(57) ABSTRACT

A system and method for enrolling patients in a medical study, includes: a database component operative to maintain a medical practice database component and their corresponding plurality of specialities and a clinical studies database component and their corresponding plurality of medical studies. The system further includes a communications component to alert the medical practices of the medical studies and observe changes to the database components. The system also includes a processor programmed to update the database components, periodically match compatible medical specialties with the medical studies, and generate reports of the matched medical practices in the medical practice database. The system also includes a fee database component which the processor uses to calculate a fee for conducting the study.

14 Claims, 3 Drawing Sheets

SYSTEM AND PROCESS FOR MATCHING PATIENTS WITH CLINICAL MEDICAL TRIALS

TECHNICAL FIELD

This invention relates generally to the field of clinical drug and device trials and more specifically to a process for obtaining patients for these trials and for pricing the value of the enrolled patients and processing payment to screening physicians.

BACKGROUND ART

As the number of elderly people increase in the United States and their lifespans extend there is an ever increasing need for newer and safer pharmaceutical products. As such, there is a need for new drugs and medical devices to be approved more rapidly. With the mapping of the human genome it is estimated that drug targets and drugs will multiply tenfold, necessitating more clinical testing. In fact, The Pharmaceutical Research and Manufacturers of America (PhRMA) states that all drugs currently on the market are based on about 500 different targets. They expect this number to increase 600-2000%, to 3,000 to 10,000 drug targets in the coming years. However, such medical advances are outrageously expensive and have necessitated changes throughout the industry.

It is estimated to cost $880 million to bring one new drug to market. And it is estimated that the average pharmaceutical company has 70 new drugs in development. This has forced the pharmaceutical companies to consolidate for the purpose of underwriting the prohibitive expense of bringing a drug to market. The average drug takes 10 to 12 years to bring to market and must negotiate a series of 3 clinical trials before approval by the Food and Drug Administration (FDA) can even be granted, leaving 8 to 10 years on a drug patent to recoup costs and turn a profit. Factoring in the governmental and managed care cost containment pressures, the pharmaceutical companies must produce one blockbuster medicine every 18 months to survive.

In summary, the pharmaceutical companies are in a position where they are producing more new drug compounds than ever before; they are about to lose the patents on many of their highly profitable, blockbuster, drugs; and they are being squeezed by the managed care industry. It is therefore critical for the pharmaceutical companies to discover, test and market the maximum number of new drugs in the minimum amount of time.

In order to speed up this process, business efficiencies are being applied to the previously haphazard clinical trials process. According to a Tufts University study, each day a study is late a pharmaceutical company can lose $1.3 million in lost prescription drug sales and it can be as high as $10 million for a blockbuster drug. Clinical trials are for the most part paper-based; necessarily cumbersome; and slow to monitor, process and store. One of the key factors affecting the time it takes to complete a clinical trial or study is the time it takes to recruit, screen and refer patients to the study. Only when the study is completely populated with patients can testing begin. Currently, the haphazard methods to recruit patients can take up to a year and thus, it becomes no surprise that 75% of all clinical studies are completed late.

There are a number of web-based clinical trial management software programs which plan, administer, and process trials for pharmaceutical companies. Although less than 15% of drug trials are e-clinical trials, this number is expected to increase to 50% or more in the next few years. Such trials will allow realtime monitoring of trials for adverse drug reactions and quality control, as well as more efficiently, move and process the prodigious amount of data generated. However, one area which still has not been adequately addressed is recruitment.

Traditionally, patients for studies have been enrolled from an investigator's clinic or practice, via referrals or by advertising. The only known prior art publication that addresses this problem is entitled Recruiting A Patient Into A Clinical Trial, Pub. No. US 2002/0099570 A1 by Knight. Basically, Knight discloses how a patient with a particular disease may find a relevant study using a computer, a web browser and Internet connection. Otherwise, the need for recruiting patients is served by databases of patients available for drug trials, or by programs that flag key words on dictated summaries using a search engine for evaluation for eligibility in studies, or by web-based patient enrollment programs. There are a number of websites where patients may do a preliminary application for eligibility and thereby enroll by this means.

The known prior art does not systematically search all available places that patients may be found for drug trial enrollments. In particular, those websites that deal only with investigators comprise only 5% of all physicians, and a corresponding number of patients. Knight's method does not systematically search for and find patients. It is believed that none of the known systems have a way to tap into and motivate the 95% of non-research performing physicians to find and enroll their patients into studies. And the known systems depend on patients having a computer with internet access. The method that searches dictations and flags patients is basically used in the offices of physicians with large practices who do research. These physicians are then paid for each patient found and for administering the study on that patient. However, these physicians are usually specialists who depend on referrals and it may take months for newly diagnosed patients to see the specialist.

Therefore, based upon the foregoing, there is a need for a process that will tap a larger pool of patients more systematically, and that will identify prospective patients at an earlier stage of their ailment before they see the appropriate specialist. And there is also a need to accurately estimate the cost of doing the study and distribute payments to the participating physicians.

SUMMARY OF THE INVENTION

In light of the foregoing, it is a first object of the present invention to provide a system for enrolling patients in a medical study, comprising: a database component operative to maintain a medical practice database component and their corresponding plurality of specialities and a clinical studies database component and their corresponding plurality of medical studies; a communications component to alert said medical practices to said medical studies and observe changes to said database components; and a processor programmed to: update said database components: periodically match compatible medical specialties and medical studies; and generate reports to matched medical practices in said medical practice database.

It is another object of the present invention to provide a computerized method for matching patients to clinical medical studies, comprising: identifying a group of medical practices; identifying at least one clinical study; maintaining a database identifying each said medical practice and each said clinical study; and comparing said medical practices and said clinical studies and matching one to the other.

BRIEF DESCRIPTION OF THE DRAWINGS

For a complete understanding of the objects, techniques and structure of the invention, reference should be made to the following detailed description and accompanying drawings, wherein.

BEST MODE FOR CARRYING OUT THE INVENTION

Figure 1:
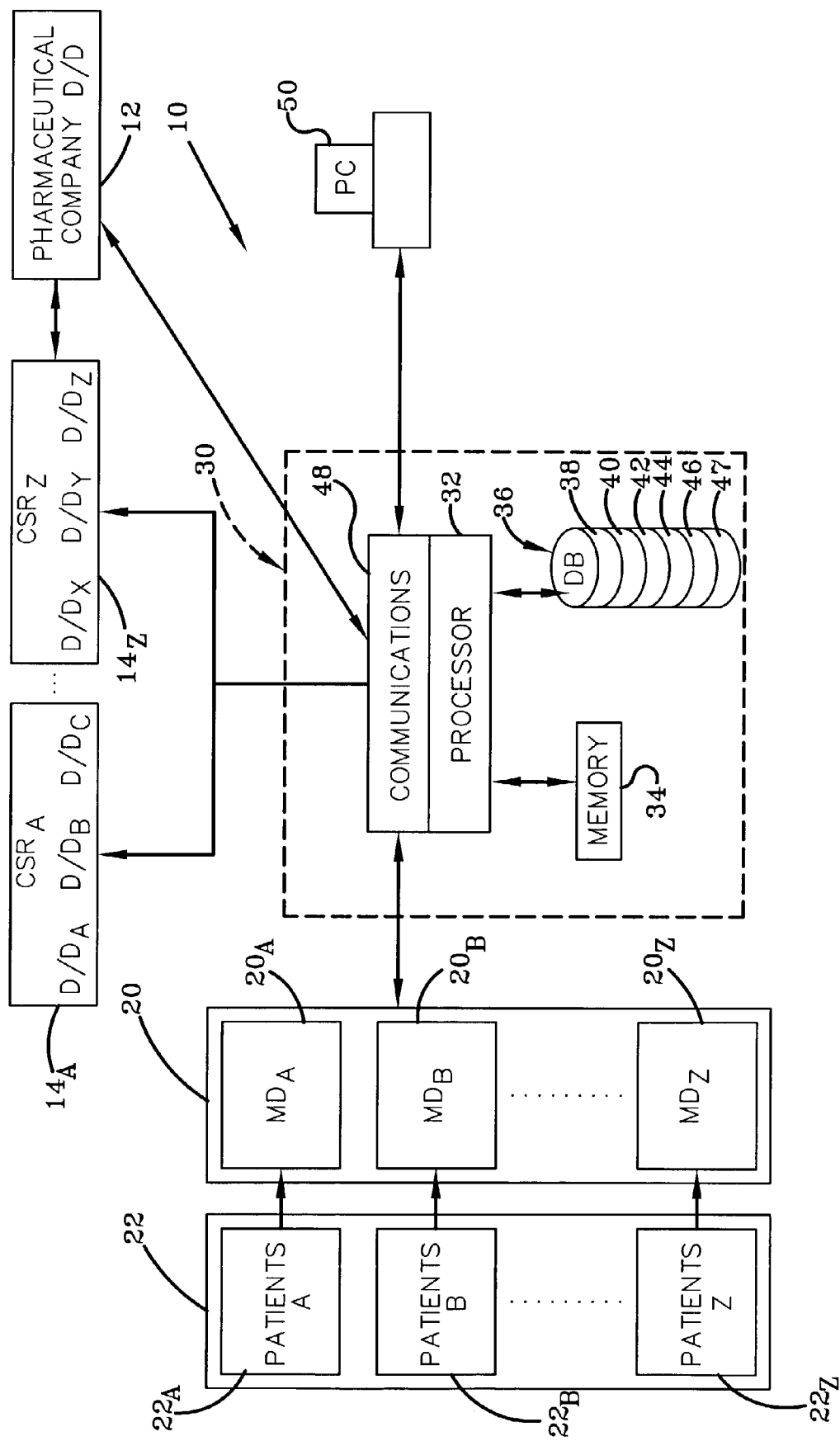
FIG. 1 is a schematic diagram of the system according to the present invention.

Referring now to FIG. 1, it can be seen that a system and related method for enrolling patients in a medical study is designated generally by the numeral 10. The system 10, includes various organizations or entities that cooperate with one another to enroll patients in a medical study, provide results of the study, and distribute payments for services rendered. In particular, the system 10 includes a pharmaceutical or medical device company designated generally by the numeral 12. As discussed previously, pharmaceutical companies and medical device manufacturing companies are required to assure the consuming public that the drugs and/or devices that they manufacture are safe for use and/or consumption and that they have no adverse consequences resulting from their use. In order to obtain an independent evaluation of the drug or medical device, the pharmaceutical company 12 contracts with an entity identified by the initialism CSR 14. It will be appreciated that the pharmaceutical companies may contract a study for a particular drug or device with various CSRs and as such they are designated with an appropriate alphabetic suffix. A CSR 14 may be an entity such as a Contract Research Organization which procures drug trial contracts so that they can either perform the trials themselves, or outsource it; a Site Management Organization which manages multiple research sites, inasmuch as these organizations do research at multiple places or facilities; or a Researcher which may be an individual doctor or medical professional, either individually or in a group, that does research as a part of their professional medical services. Accordingly, a CSR may be any entity that does studies and hence has a need to recruit patients or subjects for these studies.

Another set of participants in the system 10 are medical practices designated generally by the numeral 20 wherein any number of specific medical practices are provided with a alphabetic suffix. Accordingly, the system 10 is adaptable to receive input from various types of medical practices. For example, medical practice 20A may be a medical practice specializing in dermatology, while medical practice 20B may be a medical practice specializing in cardiology. Likewise, medical practice 20Z may be a hospital practice that specializes in emergency medicine. Each medical practice 20 has associated therewith a patient clientele designated as 22 with a corresponding alphabetic suffix associated with the alphabetic suffixes of the medical practice 20.

A CSR 14 may be requested to evaluate a drug or device, which is designated in the drawings as D/D, wherein different drugs or devices are provided with a different alphabetic suffix as deemed appropriate by the CSR 14. The CSR 14, in conjunction with the pharmaceutical company 12, prepares a study profile 18. As will be discussed in further detail, the study profile 18 sets out protocols and/or eligibility criteria which are submitted to a coordinator designated generally by the numeral 30. If desired, the pharmaceutical company 12 may directly establish a relationship with the coordinator 30 for the purpose of obtaining prospective patients for a clinical study.

The coordinator 30 is an entity that assists the CSRs 14 in finding patients that meet the eligibility requirements established by the pharmaceutical companies for the drug or device 16. The coordinator 30 is capable of receiving and sending communications in any number on forms, including, but not limited to facsimile, page, email, voice text, website data entry and instant messaging. The coordinator 30 includes a computer processor 32 which includes the necessary hardware, software and memory to implement the system and methodologies disclosed herein. The processor 32 is programmed to coordinate all activities of the system such as routing messages, performing searches generating billing statements and facilitating the clinical study process. Moreover, the processor 32 provides access to a database designated generally by the numeral 36. The processor 32 also formats the contents of the database and allows for changes, additions, or deletions to the database records as needed. As will be discussed in further detail, the database 36 has several database components including, but not limited to, a clinical study database component 38, a doctor database component 40, a patient database component 42, a doctor's fees database component 44, an ancillary fees database component 46, and a CSR database component 147. All the database components are readily accessible by the processor and are searchable by key words or as deemed appropriate. The processor 32 also provides a communications component 48 which allows for direct electronic or voice communications between the CSR 14, the medical practices 20 and the coordinator 30. The database 36 is structured to efficiently allow for the searching of various data attributable to the patients 22, the medical practices 20 and the clinical study eligibility requirements associated with a particular drug or device 16.

The clinical study eligibility requirements 18 that are loaded into the database component 38 may include, but are not limited to, the age and gender of the prospective patients, their height, weight, genetic characteristics including specific DNA samples or markers, blood pressure ranges, blood sugar levels, and the like. The doctor database component 40 includes, but is not limited to, the practice areas of the doctor or hospital, the number of patients in their practice, the location of their practice and the like. The patient database component 42 includes information about all of the patients associated with a particular medical practice 20 and includes their specific height, weight, age, any particular genetic markers or the like. And component 42 may include key words associated with a patient's medical history including dictations prepared by the medical professional; lab, radiology and pathological reports; blood work panels and other appropriate information. The database component 44 includes medical fees associated with relatively standard procedures that are performed by the medical professional such as blood tests, office visits, taking of vital signs, supervising and preparing a specific type of medical history, performing a medical physical and the like. The ancillary fee database component 46 is associated with preparation of reports and other activities by personnel within the doctor's office, mailing charges and the like. The CSR database component 47 would keep on accounting for the coordinator 30 of which CSRs received which patients and how much the CSR has paid to the coordinator.

At least one personal computer 50 may be linked to the coordinator 30 to allow for searching of the various database components and linking to other computers on a network or via the internet.

Figure 2:
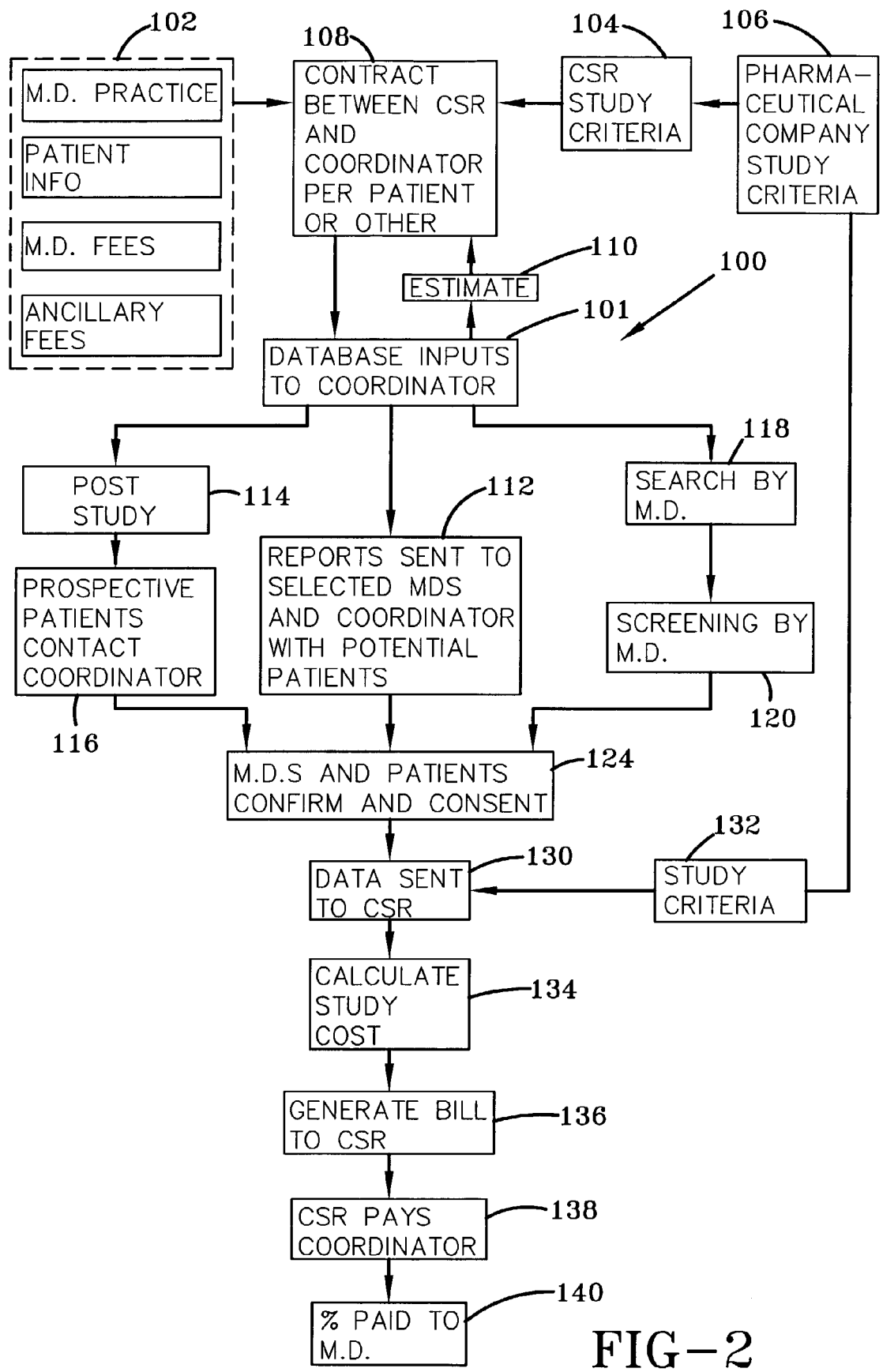
FIG. 2 is a flowchart of the process according to the present invention.

Referring now to FIG. 2, the process which is used in implementing the system 10 is designated generally by the numeral 100. The process 100 utilizes the following steps for matching patients to clinical studies. In particular, at step 101, the database inputs are made to the coordinator 30. In particular, at step 102, the information regarding the medical practice, the patients, the doctor fees and the ancillary fees are submitted to the processor 32 for loading into the database 36. Likewise, the CSR 14, or the pharmaceutical company 12, inputs to the database, at step 104, study criteria eligibility and related information proffered by the pharmaceutical company, at step 106, to the CSR. Alternatively, the pharmaceutical company 12 inputs directly the study eligibility criteria to the database.

In order to properly understand the relationships between the primary entities, a brief review of these relationships will be discussed. As noted previously, the pharmaceutical company or medical device manufacturer 12 needs to obtain test data regarding their respective drugs or devices D/D to comply with Food and Drug Administration regulations and to assure the general consuming public that the new drugs or devices which they have developed are safe for use. Accordingly, in exchange for test data obtained by these clinical studies, pharmaceutical companies and device manufacturers will pay a predetermined amount of money to a CSR. The CSR 14 will have already entered into either a fixed fee or per patient arrangement contract, at step 108, with the coordinator 30 so that the CSR can deliver the requested information to the pharmaceutical company while the coordinator obtains the necessary patients or clientele required by the CSR to complete the study. Prior to entering into a contract, the coordinator 30 will likely generate an estimate per patient, at step 110, derived from the database components inputs provided previously by the medical practices, the proposed study protocols, and a percentage mark-up for the coordinator. Accordingly, if the estimate is within the budget of the pharmaceutical company, the CSR 14 in turn will contract with the coordinator 30 for them to provide the patients for the study.

Upon completion of step 101, several methodologies may be employed for obtaining the necessary patients for the study requested by the pharmaceutical company. In the preferred embodiment, the coordinator 30 generates a report, at step 112, wherein the processor 32 matches the study information eligibility requirements in database component 38 with the medical practice database component 38 stored on the database 36. In particular, the matching report will also include a listing of the patients 22 that potentially fulfill the requirements of the study requested by the pharmaceutical company and this report will be sent directly to the doctor or medical practitioner and the coordinator. Alternatively, at step 114, the study eligibility requirements may by posted on an internet site by the coordinator, or alternatively advertised in professional journals, newspapers, or magazines that reach the target audience for the study. At step 116, prospective patients may then contact the coordinator 30 directly and submit their medical information via the communications component 48 associated with the processor. In another alternative, a medical practitioner, who may or may not be part of a medical practice included in the database component 40, may search the coordinator's website, at step 118, by inputting particular search words that afflict a particular patient that medical practitioner may know of. At step 120, the medical practitioner screens and flags the studies that may be of assistance to their particular patient and contacts the coordinator 30. This may be done manually by just reviewing a listing of the searches or it may be done by inputting key words.

In any event, upon completion of step 112, the communications component of the coordinator 30 is utilized and the medical practices 20 confirm and obtain the consent of the prospective patients to affirm that they match the criteria requested by the pharmaceutical company and to obtain all the necessary release forms from the patients so that they understand the risks and potential benefits of being part of the study. Upon completion of step 124 the appropriate data is sent to the CSR and upon receipt of the appropriate number of patients for the study, the study may be commenced. It will be appreciated that, at step 132, the specific study protocol is provided by the pharmaceutical company and any final changes or adjustments made between the contracting step and the step of initiating the actual study is likely confirmed and verified.

At step 134, the study is initiated and the coordinator 30 calculates a study cost or price per patient for performing all the necessary office visits to obtain the necessary reports resulting from the various procedures such as blood screening and testing, dispensing of the medication to be evaluated, or the device to be analyzed. Also included in the calculation of the costs are stipends for the patients and any related secretarial or office visit charges. Once these procedures are performed and the costs are submitted, a bill is generated, at step 136, by the coordinator 30 and sent to the appropriate CSR 16.

At step 138 the CSR will pay the coordinator 30 the appropriate amount and at step 140 the coordinator takes a certain percentage of the payment to cover their costs associated for maintaining the processor and the database information, and the remaining funds are paid to the appropriate medical practice to cover their costs.

Figure 3:
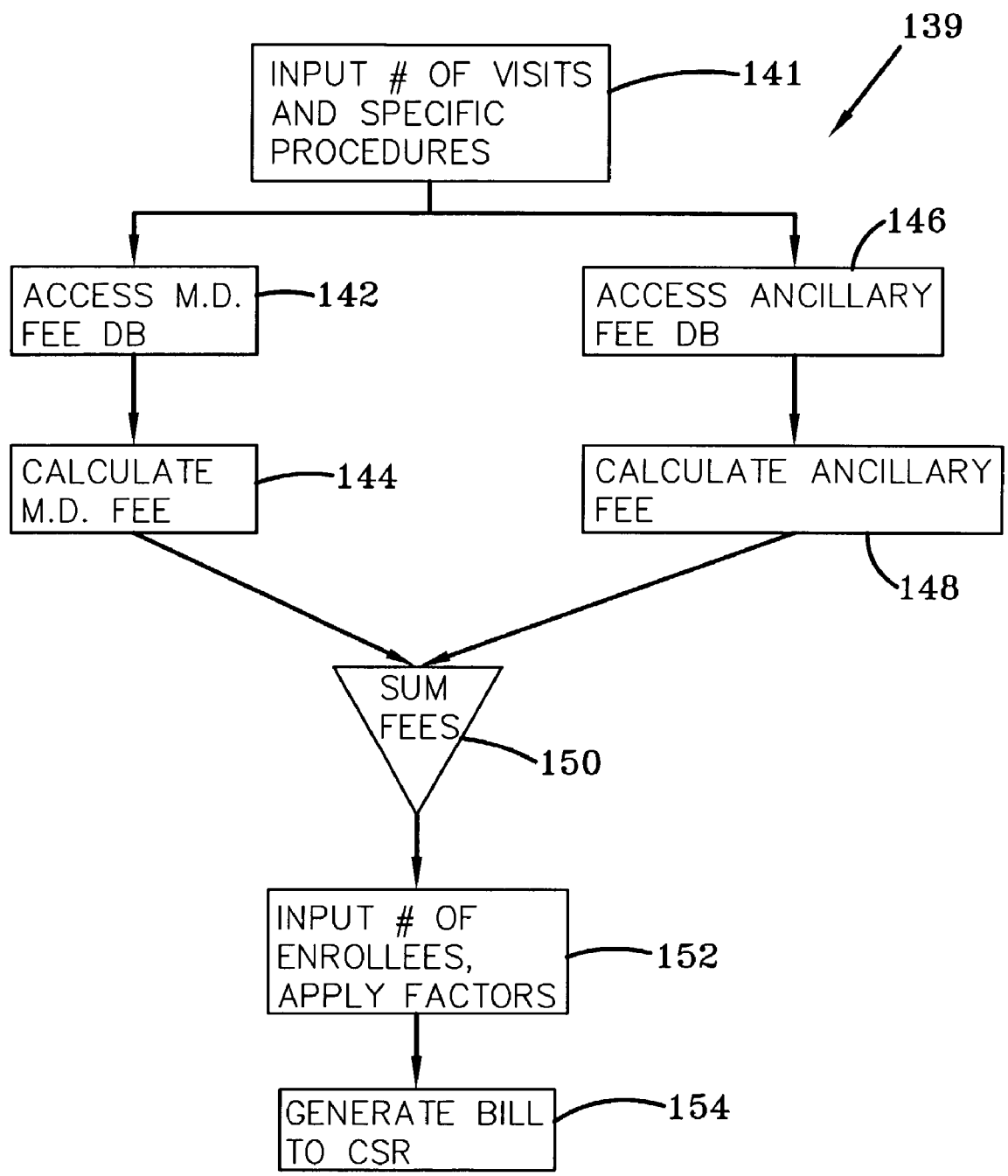
FIG. 3 is a flowchart of the process used in determining a cost per patient enrolled in a clinical trial.

Referring now to FIG. 3 of the drawings and to the Example below, a detailed explanation of the cost calculation step 134 will be discussed in detail. At step 141 the number of visits and specific procedures to be performed in a particular study are input into a calculator maintained by the processor. Subsequently, at step 142, the processor accesses the doctor fee database and at step 144, calculates a doctor fee for a particular study. At step 146 the processor accesses the ancillary fee database for the same study and calculates the ancillary fees at step 148. At step 150 the calculated fees are summed to generate a total dollar value for the study. At step 152 the number of patients enrolled in the study are input and various other factors may be applied according to the location of the medical practice and various cost differentiations that may occur, especially if the studies are conducted on a national level. In any event, the coordinator generates a bill at step 154 that is submitted to the CSR. As discussed previously, upon payment of the bill by the CSR, the appropriate funds are distributed between the various medical practices, the patients and the coordinator 30.

EXAMPLE

| Schedule | | | | |
|---|---|---|---|---|
| Study visit | 1 | 2 | 3 | 4 |
| Study week | 2 | 4 | 6 | 8 |
| Informed consent | X | | | |
| Medical history | X | | | |
| Physical examination | X | | | |

-continued

| Schedule | | | | |
|---|---|---|---|---|
| Vital signs | X | X | X | X |
| Electrocardiogram | X | X | | |
| Fasting blood specimen | X | X | | |
| Pregnancy test | X | | | |
| 24-hour Holter Monitor | | X | X | |
| Study medications given to patient | | X | X | |
| Adverse event assessment | | X | X | X |

VISIT ONE

| | | |
|---|---|---|
| Medical history: | Done by the physician. | $125 |
| Medical physical: | Done by the physician | $125 |
| Assistant time: | Vital signs, secure the informed consent, etc. Can be done by Physician's Assistant, Nurse Practitioner or Nurse. | $75 |
| Electrocardiogram: | | $100 |
| Blood draw: | Assumes a protocol requiring the blood sample to be shipped to a central laboratory. Additional fees apply if the site sends the blood draw to its own laboratory | $25 |
| Pregnancy screen: | Urine pregnancy test in office with testing material supplied by the sponsor. | $25 |
| Additional charges: | Office visit: | $100 |
| | Secretarial charge for visit: | $25 |
| | Patient stipend: | $35 |
| Total charges for visit one | | $635 |

VISIT TWO

| | | |
|---|---|---|
| Assistant's fees | Add $25 for Physician if done by Physician | $100 |
| Visit | | $100 |
| Secretary | | $25 |
| 24 hour Holter monitor | Sponsor. Supplies the monitor $200 charge reflects the time will take the coordinator to apply the instrument and to instruct patient | $200 |
| Patient stipend | The higher stipend for this visit is due to the requirement that the patient wear the monitor, which is uncomfortable, for 24 hours. | $150 |
| Total charges for visit two | | $575 |

VISIT THREE

The requirements for visit three are the same as for visit two.
Total charges for visit three  $575

VISIT FOUR

| | |
|---|---|
| Physical | $100 |
| Electrocardiogram | $100 |
| Assistant | $ 75 |
| Office Visit | $ 75 |
| Secretary | $ 25 |
| Patient Stipend | $ 35 |
| Total Charges for Visit Four | $435 |

Total per-patient fees for the four-visit study:

| | |
|---|---|
| Visit one . . . | $635 |
| Visit two . . . | $575 |
| Visit three . . . | $575 |
| Visit four . . . | $435 |

-continued

| | |
|---|---|
| Total . . . | $2220 |
| $2,220 per patients times 16 | $35,520 |
| 15% Overhead | $5,328 |
| IRB [Institutional Review Board] | $1,500 |
| Advertising Allowance | $1,200 |
| Total | $43,548 |

Taking the total of the studies $1,200 is subtracted out in advertising and calculate 20% of $42,348 which is $8,469.60. Divide this by 16 (for 16 patients in this study comes out to $529.35 per patient. As can be seen, studies which require more office visits and procedures are more costly. The Institutional Review Board and 15% overhead are usual fees and should be calculated into the total to make sure the study is profitable for the medical practice so as to encourage them to participate in the system 10.

Based upon the foregoing, the advantages of the present invention are readily apparent. In particular, the system and related methods describe an automated process for identifying the patients and pricing their participation in the study accordingly. The system and methods also facilitate the enrolling of patients in studies and provide for a way to obtain payment for the services rendered. The primary advantage of such a system is that it will be able to draw from the practices of a vast number of physicians who are not currently involved in research and have no organized way to help patients who desire the latest medications and devices when all other alternatives have been exhausted. Accordingly, the present invention vastly widens the pool of available patients for studies, improves the accuracy of the study, and reduces the overall cost of providing a study inasmuch as an adequate number of qualified patients are quickly found for the study so that the study may be implemented on a timely basis. The present invention also provides an organized and rapid method to automatically enroll patients which helps the pharmaceutical company streamline their clinical trial processes. Moreover, the present invention is advantageous inasmuch as the pharmaceutical companies have exposed a wider number of medical practices to the potential new drugs or devices which they manufacture and this helps their marketing campaign if the drug or device is ultimately approved.

While the invention has been described in connection with a preferred embodiment, it is not intended to limit the scope of the invention to the particular form or methodology set forth, but it is intended to cover such alternatives, modifications, and equivalence as may be included within the spirit and scope of the invention as defined by the attached claims.

What is claimed is:

1. A system for finding patients suitable for enrollment in a clinical study from a plurality of medical practices, the clinical study being conducted by one of a plurality of clinical study entities, comprising:
a database component, maintained by a coordinator, operative to maintain and to store a medical practice database component having a plurality of medical practices each identified by a corresponding specialty, a clinical studies database component and their corresponding plurality of clinical studies, a patient database component having a plurality of patient records, each of said plurality of patient records identifying a patient and the patient's association with at least one of said plurality of medical practices in said medical practice database component, and a fee database component identifying fees associated with referral procedures performed by the coordinator;

a communications component, coupled to the plurality of clinical study entities and to the plurality of medical practices through a communications link, to alert said medical practices to the existence of said clinical studies, to alert said clinical study entities to the existence of said medical practices, to alert said clinical study entities and said medical practices to the existence of patients suitable for enrollment in a clinical study based upon information from said database components and to receive changes to said database components; and a processor, maintained by the coordinator, coupled to said communications component and to said database component, programmed to update said database components, to match at least one of said plurality of medical practices with at least one of said plurality of clinical studies, to interrogate said patient database component to identify data that indicate patients who may be suitable for said clinical studies, wherein said interrogation includes searching for key words embedded in the patient database records, to match patients suitable for enrollment with said medical studies based upon information from said database components, to generate a report of medical practices matched to said clinical studies, to generate a report of patients matched to said clinical studies, to inform said communications component of said reports so as to alert said medical practices associated with said matched patients, and to calculate, utilizing said fee component database, a fee to be paid to said coordinator for referral procedures performed in referral of said matched patients to said clinical study to which said patient is matched;

wherein said communications component sends at least one of said reports over said communications link to said medical practices in said medical practice database to alert said medical practices of said matched patients for referral;

wherein said medical practices find and refer said matched patients to said clinical study to which each said patient is matched; and wherein said medical practices alert said clinical study entities of referral of said patients to said medical studies over said communications link utilizing said communication component, and said database components are updated utilizing said processor.

2. The system according to claim 1, further comprising:

a posting component for listing each said clinical study in said clinical studies database component;

wherein said communications component is adaptable to receive queries from prospective patients via said posting component.

3. The system according to claim 1, further comprising;

a searching component for searching said clinical studies database and said medical practice database;

wherein said communications component is adaptable to receive queries from said medical practices and said clinical studies via said searching components.

4. The system according to claim 1, wherein said fee database component is further operative to maintain a doctor's fee database component identifying fees associated with doctor's procedures as part of said medical studies and an ancillary fee database component identifying fees associated with miscellaneous charges associated with said medical studies; and wherein said processor is programmed to calculate said fee from said doctor's fee database component and said ancillary fee database component.

5. The system according to claim 4, wherein said processor is programmed to automatically generate a billing statement based upon said fee and a number of patients actually enrolled in one of said plurality of said clinical studies.

6. The system according to claim 1, wherein said communications link comprises at least one of a network and internet.

7. The system according to claim 1, wherein said communication link is adapted to send or receive at least one of facsimile, email, voice text, website data entry and instant messaging.

8. A computerized method for finding and matching a plurality of patients from a plurality of medical practices, each having an identified specialty, who are suitable for enrollment in at least one clinical study from a plurality of clinical studies, the plurality of medical practices being coupled, through a communication component, to a plurality of clinical study entities providing the clinical studies, the method comprising:

storing medical practice data in a database, the medical practice data identifying the plurality of medical practices each having the identified specialty;

storing patient profile data in a database, the patient profile data identifying the plurality of patients each being associated with at least one of the medical practices;

storing fees in a database, said fees being associated with referral procedures performed by a coordinator;

automatically matching said medical practice data to the plurality of clinical studies to identify medical practices whose patients may be suitable for the clinical studies;

automatically matching said patient profile data of the identified medical practices to the plurality of clinical studies to identify patients who may be suitable for the clinical studies, wherein said matching includes searching for key words embedded in the patient profile data;

generating a report of the matching patient profile data;

sending the report, through the communications component, to the identified medical practice associated with the matching patient profile data that said patient of the matching patient profile meets the requirements of, and the patient's suitability for enrollment in the clinical study; and calculating a fee, using said stored fees, to be paid to said coordinator for generation of the report of the matching patient profile data.

9. The method according to claim 8, further comprising:

confirming participation of said patient matched in said sending step in one of said clinical studies.

10. The method according to claim 9, further comprising:

maintaining on said database costs incurred by each said medical practice in performing procedures specified by said clinical study; and calculating a cost for performing said procedures.

11. The method according to claim 10, generating and sending a billing statement to an entity responsible for initiating or performing said clinical study.

12. The method according to claim 9, further comprising:

maintaining on said database doctor costs and ancillary costs incurred by said medical practices in performing procedures specified by said clinical studies;

calculating a cost for coordinating and performing said procedures;

generating and sending a billing statement to entities responsible for initiating or performing said clinical studies; and determining a percentage of costs attributable to the coordinator and to said medical practices performing said clinical studies.

13. The method according to claim 8, further comprising:

maintaining on said database costs for performing procedures typically specified by said clinical studies;

inputting to said database procedures required by said clinical studies; and estimating a cost for implementing said procedures specified by said clinical studies.

14. The method according to claim 8, comprising:

searching on a network accessible by said clinical study entities and said medical practices for prospective patients suitable for enrollment in a prospective clinical study; and communicating interest of said clinical study to said medical practice in said prospective patients and interest of said prospective patients in said clinical study by said prospective medical practices to a coordinator.

* * * * *